(12) United States Patent
Nogami et al.

(10) Patent No.: US 7,714,166 B2
(45) Date of Patent: May 11, 2010

(54) PROCESS FOR PRODUCING CARNITINAMIDE

(75) Inventors: Genki Nogami, Niigata (JP); Hideo Ikarashi, Niigata (JP); Shinyo Gayama, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/992,831

(22) PCT Filed: Aug. 24, 2006

(86) PCT No.: PCT/JP2006/316597

§ 371 (c)(1),
(2), (4) Date: Mar. 28, 2008

(87) PCT Pub. No.: WO2007/037082

PCT Pub. Date: Apr. 5, 2007

(65) Prior Publication Data

US 2009/0143616 A1 Jun. 4, 2009

(30) Foreign Application Priority Data

Sep. 28, 2005 (JP) ............................. 2005-282682

(51) Int. Cl.
 *C07C 231/00* (2006.01)
(52) U.S. Cl. ..................................................... 564/126

(58) Field of Classification Search ....................... None
See application file for complete search history.

(56) References Cited

U.S. PATENT DOCUMENTS 3,366,639 A    1/1968  Haefele
5,276,185 A *  1/1994  Karasawa et al. ........... 564/126

FOREIGN PATENT DOCUMENTS

| EP | 166901 A1 * | 1/1986 |
|----|----|----|
| GB | 1075562 A | 7/1967 |
| JP | 61-1649 A | 1/1986 |
| JP | 5-170720 A | 7/1993 |

* cited by examiner

*Primary Examiner*—Paul A Zucker
(74) *Attorney, Agent, or Firm*—Fitch, Even, Tabin & Flannery

(57) ABSTRACT

A process for producing carnitinamide which is an intermediate for production of L-carnitine is provided, which can hydrate carnitine nitrile to form carnitinamide with high selectivity, whereby highly-purified carnitinamide excellent as a substrate for stereoselective hydrolysis by optical resolution or a microorganism is produced in high yield. The process comprises hydrating carnitine nitrile to form carnitinamide using a catalyst containing a manganese oxide, and thus carnitinamide substantially free from by-produced carnitine is produced in high yield, so that carnitinamide of extremely high purity can be obtained through simple and easy crystallization operation.

4 Claims, 1 Drawing Sheet

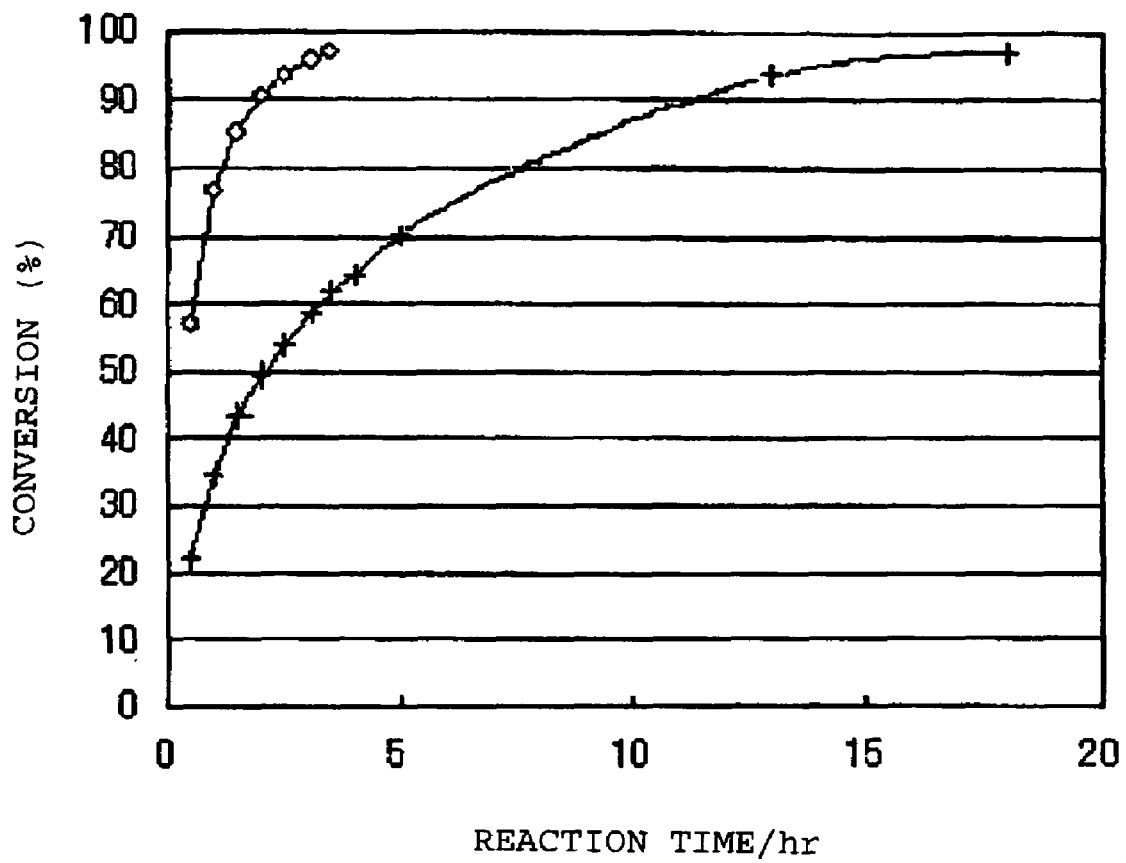
Figure 1: TIME-COURSE CHANGE OF CONVERSION (BATCH REACTION)
+————+ : The case where a commercially available manganese dioxide was used as a catalyst.
O————O : The case where a modified manganese dioxide containing vanadium was used as a catalyst.

PROCESS FOR PRODUCING CARNITINAMIDE

CROSS-REFERENCE TO RELATED APPLICATION

This is a U.S. National Phase of International Application PCT/JP2006/316597, filed Aug. 24, 2006, and claims the benefit of foreign priority under 35 U.S.C. §119 based on JP 2005-282682, filed Sep. 28, 2005, the entire disclosures of which applications are hereby incorporated herein by reference.

TECHNICAL FIELD

The present invention relates to a process for producing carnitinamide from carnitine nitrile, and more particularly, relates to a catalyst composition which is used when carnitinamide is produced by hydration reaction of carnitine nitrile. Carnitinamide is an intermediate for producing L-carnitine which is used as a supplement and is pharmaceutically important.

BACKGROUND ART

As processes for producing carnitinamide from carnitine nitrile, those using concentrated hydrochloric acid or hydrogen peroxide as a reaction catalyst are known (see, for example, Patent Documents 4, 5 and 6). In any of these processes, however, it is extremely difficult to terminate the hydration reaction of the nitrile group just at a stage of carboxylic amide which is easily converted into carnitine due to further hydration, or crotonobetaine due to hydration and dehydration that occur in conjugation with each other. In order to isolate carnitinamide from such a reaction solution containing a large amount of by-products, it is necessary to employ a complicated purification procedure involving multiple steps, or allow the purity to deteriorate in exchange for simplification of the process.

On the other hand, as processes for separating optically active L-carnitine from racemic carnitinamide, a process in which L-carnitinamide is converted into L-carnitine by stereoselective hydrolysis using a microorganism and is separated from the remaining D-carnitinamide (see, for example, Patent Documents 1 and 2); and a process using D-camphoric acid as an optical resolution agent (see, for example, Patent Document 3) are known. However, because the carnitine produced as a by-product at the stage where carnitine nitrile is hydrated to carnitinamide is a racemate, both of these optical resolution processes are still problematic in that optical purity and optical resolution efficiency are lowered due to the inclusion of D-carnitine in the resulting L-carnitine.

Another drawback to these techniques is that they require operations under acidic or basic conditions, and thus a large amount of salts are produced as by-products which must be separated and disposed of. As a technique for solving this problem to a certain extent, one in which hydrogen peroxide is allowed to act on carnitine nitrile using a catalytic amount of a base (see, for example, Patent Document 7) is known. However, since this technique is originally intended for synthesis of carnitine, it is difficult to suppress formation of carnitine as a by-product. Also, the technique has a drawback in that an excess amount of hydrogen peroxide is used, and thus residual hydrogen peroxide must be removed to obtain carnitinamide. Moreover, the reference describes that sodium hydroxide or potassium hydroxide is more advantageously used as a catalyst to allow the reaction to proceed well. However, because carnitinamide is a quarternary ammonium salt, it is extremely difficult to separate, after the reaction, these metal cations which adversely affect optical resolution or enzyme reactions.

It is known that various nitrile compounds can be converted into amide compounds via hydration using a catalyst containing manganese oxide (see, for example, Patent Document 9). However, none of the references including this patent document has disclosed that a catalyst containing manganese oxide is used for hydration reaction of a nitrile compound that contains a quaternary ammonium group.

Patent Document 1: Japanese Patent Laid-Open No. 4-320679
Patent Document 2: Japanese Patent Laid-Open No. 63-56294
Patent Document 3: Japanese Patent Laid-Open No. 55-13299
Patent Document 4: Belgian Patent No. 659194 specification
Patent Document 5: Japanese Patent Publication No. 38-23
Patent Document 6: Japanese Patent Laid-Open No. 61-1649
Patent Document 7: Japanese Patent No. 2588930
Patent Document 8: U.S. Pat. No. 4,070,394 specification
Patent Document 9: U.S. Pat. No. 3,366,639 specification

DISCLOSURE OF THE INVENTION

Problems to be Solved by the Invention

The object of the present invention is to establish an industrially applicable production process which can hydrate carnitine nitrile to form carnitinamide with high selectivity, so that a process for producing carnitinamide is provided which minimizes the amount of by-products such as carnitine and produces little waste such as salts.

Means for Solving the Problems

The present inventors have conducted extensive researches for achieving the aforementioned object, and have consequently found that a process in which carnitine nitrile is hydrated to form carnitinamide using a catalyst containing a manganese oxide can reduce the amount of carnitine as a by-product to several mol % or less, so that a simple crystallization procedure can be used to provide highly-purified carnitinamide which is substantially free from carnitine. This finding has led to the completion of the present invention.

Specifically, the present invention relates to a process for producing carnitinamide by way of hydration of carnitine nitrile, characterized by using, as a catalyst, a composition containing a manganese oxide, as summarized in items (1) to (4) shown below.

(1) A process for producing carnitinamide, characterized in that a carnitine nitrile represented by the following general formula (1) is hydrated in a presence of a catalyst containing a manganese oxide:

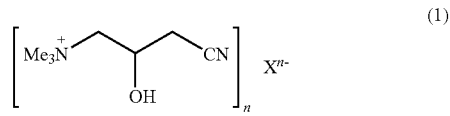

wherein $X^{n-}$ is an anion of a mineral acid or organic acid; and n is a positive integer excluding zero.

(2) The process for producing carnitinamide, according to item 1), wherein the catalyst containing a manganese oxide contains at least one element selected from the group consisting of an alkali metal element, bismuth, vanadium, and tin.

(3) The process for producing carnitinamide, according to item 2), wherein the alkali metal element comprises at least one element selected from the group consisting of sodium and potassium.

(4) The process for producing carnitinamide, according to any one of items 1) to 3), wherein $X^{n-}$ in the general formula (1) is $Cl^-$.

Effects of the Invention

According to the present invention, by-production of carnitine can be minimized during the hydration reaction of carnitine nitrile to carnitinamide. Therefore, the present invention allows the production of carnitinamide that is high in purity and substantially free from carnitine whilst purification yield is not lowered, and does not produce wastes such as salts; hence the present invention is industrially very significant.

BEST MODE FOR CARRYING OUT THE INVENTION

Hereinafter, the process according to the present invention will be described in detail. Manganese dioxide is typically used as a manganese oxide that is contained in the catalyst used in the present invention. Manganese dioxide is a manganese oxide falling between $MnO_{1.7}$ to $MnO_2$ in general, and known crystal structures thereof include α, β, γ, δ, ε, and the like. However, the crystal structures are extremely complicated and of great variety since there occur transitions between respective phases and changes in crystallinity degree. Manganese dioxide exists in nature. However, when manganese dioxide is used as a catalyst, preferably used is manganese dioxide prepared by use of either or both of a process in which divalent manganese is oxidized and a process in which heptavalent manganese is reduced.

Known examples of such processes include a process in which a permanganate compound is reduced at 20 to 100° C. in a neutral or alkaline region (Zeit. Anorg. Allg. Chem., 309, pp. 1-32 and pp. 121-150. (1961)); a process in which an aqueous solution of potassium permanganate is added to an aqueous solution of manganese sulfate (J. Chem. Soc., 2189, (1953)); a process in which a permanganate is reduced with a hydrohalic acid (Japanese Patent Laid-Open No. 63-57535); a process in which a permanganate is reduced with a polycarboxylic acid or a polyhydric alcohol (Japanese Patent Laid-Open Nos. 9-24275 and 9-19637); a process in which a permanganate is reduced with hydrazine, hydroxycarboxylic acid or a salt thereof (Japanese Patent Laid-Open No. 6-269666); and a process in which an aqueous solution of manganese sulfate is electrolytically oxidized (Japanese Patent Laid-Open No. 7-257928). The catalyst which is mainly composed of a manganese oxide and is used in the present invention may be one prepared by any of the aforementioned various processes, and is preferably a modified manganese dioxide containing an alkali metal element. A preferable process for preparing the catalyst is a process using divalent manganese and heptavalent manganese together since it can control crystal form and specific surface area as well as types or amounts of alkali metals (Japanese Patent Laid-Open Nos. 3-68447 and 3-93761). Other elements such as elements belonging to Groups 2, 3, 4, 5, 6, 8, 9, 10, 11, 12, 13, 14, and 15 of the periodic table can also be added to the manganese dioxide or the modified manganese dioxide containing an alkali metal element; and addition of an alkaline earth metal, Sc, Zr, V, Nb, Ta, Cr, Mo, W, Zn, Ga, In, Ge, Sn, Pb, or Bi are more preferable. Generally, the amount of these elements to be added is preferably 0.005 to 0.20, and more preferably 0.01 to 0.1 in terms of atomic ratio to one manganese atom. Among the metallic elements, Bi, Sn, and V are excellent in terms of activity and catalytic life, among which V is particularly excellent in terms of catalytic activity and safety of production of intermediates for pharmaceuticals and dietary foods. These metals can be added to manganese dioxide using any of processes such as impregnation, adsorption, kneading and coprecipitation, and among them, coprecipitation is particularly preferable. These preparation processes may be carried out under an acidic or basic condition, but is preferably carried out under an acidic condition. When the preparation process is carried out under a basic condition, manganese dioxide is preferably washed with an acidic solution such as dilute sulfuric acid before it is used for the reaction.

In the above-mentioned process for preparing a catalyst, divalent manganese sources include water-soluble salts among which sulfates are particularly preferable. Heptavalent manganese sources are particularly preferably water-soluble potassium permanganate or sodium permanganate, and these can also be used as an alkali metal source. Preferable sources of alkaline earth metals, Sc, Zr, V, Nb, Ta, Cr, Mo, W, Zn, Ga, In, Ge, Sn, or Pb to be added to manganese dioxide are water-soluble salts among which sulfates are particularly preferable. As a Bi source, a water-soluble salt such as bismuth sulfate or bismuth nitrate can be used, but bismuth oxide is most suitably used. The catalyst for use in the present invention can be used as it is, or can be used in a manner in which the catalyst is supported on a carrier of a metal oxide such as alumina, silica, zirconia or titania. The catalyst thus obtained is molded and used as a fixed bed catalyst, or is used in a batch reactor or continuous flow reactor as a slurry catalyst in its powdery form or after being molded into granules, microspheres or the like.

The hydration reaction is typically carried out in a system containing an excess amount of water. That is to say, concentration of carnitine nitrile in a raw material solution is typically from 3 to 80 wt %, and preferably 5 to 40 wt %. Reaction temperature is typically from 0 to 120° C., and preferably 30 to 80° C. A reaction temperature lower than the range is not preferable because rate of reaction decreases. A reaction temperature higher than the range is not preferable because the amount of by-products such as carnitine increases.

Carnitine nitrile which is shown by the general formula (1) and used in the process of the present invention can be obtained in accordance with various processes (Japanese Patent Laid-Open Nos. 61-1649, 60-231632, and 60-258487, and U.S. Pat. No. 3,135,788 specification).

As $X^{n-}$, many anions of acids can be used as far as they are not easily oxidized. Examples thereof include mineral acid anions such as $Cl^-$, $SO_4^{2-}$, $NO_3^-$, $ClO_4^-$, and the like; and various organic acid anions such as formic acid, acetic acid, propionic acid, oxalic acid, succinic acid, ascorbic acid, benzoic acid, toluenesulfonic acid, and the like. Among them, halogen ions such as $Cl^-$, $Br^-$ and $I^-$ are preferable, and $Cl^-$ is particularly preferable.

The present invention does not impose any limitation on processes for purifying carnitinamide from the hydration reaction solution. However, because the reaction solution is substantially free from impurities such as inorganic salts, carnitinamide of high purity can be easily obtained in high yield by way of concentration, crystallization, filtration and drying in accordance with an ordinary process. For example, a carnitinamide salt can be crystallized by pouring the reaction solution into a hydrophilic organic solvent such as acetone. However, this is not efficient because a large amount of an organic solvent must be used, and a layer in which the salt is dissolved is separated. More advantageously, concentration of the reaction solution is previously conducted, for example, under reduced pressure. By distilling off water at 40 to 60° C. under reduced pressure, the solution can be easily concentrated by a factor of up to about 8.5. Water may be distilled off completely. However, even if the solution is concentrated by a factor of 8.5 or higher, the amount of the organic solvent to be used cannot be reduced significantly. Rather, if the concentration factor is too high, crystal purity will be deteriorated because of contamination with carnitine nitrile and the like. In view of the above, it is desirable that the concentration factor is from 5 to 8.5, and preferably 6 to 8.

Crystallization can be conducted at 0 to 60° C. after a hydrophilic organic solvent such as methanol, ethanol and isopropanol is added to the concentrated solution in an amount of about 0.5 to 2 times by volume the concentrated solution. In this instance, crystallization should be conducted under gentle stirring so that crystals cannot adhere to the walls of the vessel, thereby facilitating the subsequent filtration procedure. Isolation of crystals can be conducted, for example, by suction-filtering the produced crystals and washing them with the same hydrophilic organic solvent as added during crystallization in an amount about one to two times the amount by volume of the solvent used during crystallization, followed by drying, to yield highly-purified carnitinamide which is substantially free from impurities such as carnitine.

When conversion from carnitine nitrile to carnitinamide is 90% or higher, carnitinamide can be obtained in a yield of 60 to 90% and at a carnitinamide purity of 99.0 to 99.9% (with the remaining 0.1 to 1% being carnitine nitrile) by concentrating the reacted solution by a factor of 6 to 8.5, adding a hydrophilic organic solvent in an amount of about 0.5 to 2 times by volume the concentrated solution, and conducting crystallization at 0 to 60° C. Since secondary crystals can be obtained by concentrating a mother liquor again after separation of primary crystals, and adding a hydrophilic organic solvent to the mother liquor to conduct crystallization, substantially the whole carnitinamide converted from carnitine nitrile can be recovered as crystals. Although secondary crystals may contain unconverted carnitine nitrile, carnitinamide having a quality equal to primary crystals can be obtained by effecting a further reaction for converting carnitine nitrile to carnitinamide, and subsequently purifying the carnitinamide by crystallization.

Meanwhile, processes for separating optically active L-carnitine from racemic carnitinamide are known, examples of which include a process in which L-carnitinamide is converted into L-carnitine by stereoselective hydrolysis using a microorganism, and then the remaining D-carnitinamide is separated by electrodialysis or with a strongly acid ion exchange resin (Japanese Patent Laid-Open Nos. 63-56294, 1-213258, and 1-213259); and a process in which racemic carnitinamide is optically resolved using a resolving agent such as D-camphoric acid, and then L-carnitine is obtained by hydrolysis using oxalic acid or the like under such conditions that racemization does not occur (Japanese Patent Laid-Open No. 55-13299). Of these examples, the process using a microorganism is superior from the viewpoint of convenience and economical efficiency.

EXAMPLES

Hereinafter, the process of the present invention will be described in detail by way of Examples and Comparative Examples; however, the invention is not limited to these examples.

Example 1

One gram (1.0 g) of a commercially available powdery manganese dioxide was added to 10 ml of a raw material solution obtained by mixing 10 wt % of carnitine nitrile chloride with 90 wt % of water. The resulting mixture was stirred and allowed to react at 60° C. in the presence of air, and time-course change of conversion of carnitine nitrile chloride was monitored. The results are shown in FIG. 1. Eighteen hours after the start of the reaction, conversion of carnitine nitrile chloride was 97.0%, and selectivity of carnitinamide chloride was 97.8% (with the remainder being carnitine hydrochloride).

Example 2

(1) Catalyst Preparation: A solution obtained by dissolving 0.316 mol of manganese sulfate monohydrate and 0.007 mol of vanadium sulfate in 200 ml of water and mixing therewith 0.968 mol of concentrated sulfuric acid was rapidly poured under stirring at 70° C. into a solution of 0.398 mol of potassium permanganate in 200 ml of water. Stirring was further continued and the mixture was aged at 90° C. for two hours, and then the resulting precipitate was filtered and washed with 2000 ml of water five times. The resulting cake was dried overnight at 110° C. to give 64 grams of a modified manganese dioxide. Contents of metal components in the modified manganese dioxide were measured, and the result was vanadium/potassium/manganese=0.01/0.09/1 (atomic ratio).

(2) Reaction: Time-course change of conversion of carnitine nitrile chloride was monitored in the same manner as in Example 1, except that 1.0 gram of the above modified manganese dioxide containing vanadium was pulverized in a mortar and the resultant powder was used. The results are shown in FIG. 1. 3.5 hours after the start of the reaction, conversion of carnitine nitrile chloride was 96.9%, and selectivity of carnitinamide chloride was 99.0% (with the remainder being carnitine hydrochloride).

Example 3

One and a half (1.5) gram of a powdery modified manganese dioxide prepared in the same manner as in Example 2 and containing vanadium was added to a raw material solution obtained by mixing 1 gram of carnitine nitrile chloride with 9 grams of water, and the mixture was allowed to react under stirring at 60.degree. C. in the presence of air. Two hours after the start of the reaction, conversion of carnitine nitrile chloride was 96.7%, and selectivity of carnitinamide was 99.7% (with the remainder being carnitine hydrochloride) (Table 1).

Example 4

One and a half (1.5) gram of a powdery modified manganese dioxide prepared in the same manner as in Example 2 and containing vanadium was added to a raw material solution obtained by mixing 1 gram of carnitine nitrile iodide with 9 grams of water, and the mixture was allowed to react under stirring at 60° C. in the presence of air. Two hours after the start of the reaction, conversion of carnitine nitrile iodide was 94.4%, and selectivity of carnitinamide was 99.7% (with the remainder being carnitine iodate) (Table 1).

Example 5

One and a half (1.5) gram of a powdery modified manganese dioxide prepared in the same manner as in Example 2 and containing vanadium was added to a raw material solution obtained by mixing 1 gram of carnitine nitrile sulfate with 9 grams of water, and the mixture was allowed to react under stirring at 60° C. in the presence of air. Two hours after the start of the reaction, conversion of carnitine nitrile sulfate was 88.2%, and selectivity of carnitinamide was 99.1% (with the remainder being carnitine sulfate) (Table 1).

Example 6

One and a half (1.5) gram of a powdery modified manganese dioxide prepared in the same manner as in Example 2 and containing vanadium was added to a raw material solution obtained by mixing 1 gram of carnitine nitrile nitrate with 9 grams of water, and the mixture was allowed to react under stirring at 60° C. in the presence of air. Two hours after the start of the reaction, conversion of carnitine nitrile nitrate was 95.1%, and selectivity of carnitinamide was 99.4% (with the remainder being carnitine nitrate) (Table 1).

Example 7

One and a half (1.5) gram of a powdery modified manganese dioxide prepared in the same manner as in Example 2 and containing vanadium was added to a raw material solution obtained by mixing 1 gram of carnitine nitrile acetate with 9 grams of water, and the mixture was allowed to react under stirring at 60° C. in the presence of air. Two hours from the start of the reaction, conversion of carnitine nitrile acetate was 90.7%, and selectivity of carnitinamide was 99.1% (with the remainder being carnitine acetate) (Table 1).

Comparative Example 1

(1) Reaction: 60 grams of carnitine nitrile chloride was added to 120 ml of concentrated hydrochloric acid, and the mixture was allowed to react under stirring at room temperature in the presence of air. 24 hours after the start of the reaction, conversion of carnitine nitrile chloride was 91.8%, and selectivity of carnitinamide was 85.1% (with the remainder being 14.3% of carnitine hydrochloride and 0.6% of other impurities).
(2) Purification: The reaction solution was cooled at 0° C. for 30 minutes, and then 60 ml of isopropanol was added, followed by addition of 60 ml of acetone. The resulting mixture was allowed to stand at 0° C. for one hour, and then filtered and washed (with 100 ml of isopropanol:acetone = 1:1). The resulting product was dried in vacuo at 40° C. for 12 hours. As a result, 32.8 grams (yield: 48%) of carnitinamide chloride with a purity of 97.5% (with the remainder being 2% of carnitine and 0.5% of carnitine nitrile chloride) was obtained (Table 1).

Example 8

(1) Reaction: A glass reaction tube with an inner diameter of 10 mm, equipped with a jacket, was filled with 3.0 grams of a modified manganese dioxide containing vanadium, which was prepared in the same manner as in Example 2 and was uniformly pulverized and classified to have 10 to 20 mesh. Hot water at 60° C. was passed through the jacket. A raw material solution obtained by mixing 10 wt % of carnitine nitrile hydrochloride with 90 wt % of water was passed through the reaction tube at a flow rate of 3.0 g/hr. 24, 120, 210 and 600 hours after the start of passing the solution, conversion of carnitine nitrile chloride of the solution at the outlet of the reactor were 93.2, 91.7, 90.5, and 86.2%, respectively, and selectivity of carnitinamide thereof was 98.5, 98.3, 98.4, and 99.5%, respectively (Table 2).
(2) Purification: The total 610 grams of the above reacted solutions from 0 through 210 hours were concentrated with an evaporator at 30 mmHg and at 40 to 50° C. When the weight of the melted residue reached 82.4 grams, 80 ml of 95% ethanol was added thereto, and the mixture was slowly stirred for 30 minutes while being heated to 50° C., so as to allow crystals to be precipitated. The mixture was allowed to stand at room temperature for two hours, and then at 5° C. for 16 hours so as to effect crystallization, and the resulting crystals were filtered and washed (with 200 ml of 95% ethanol), followed by drying in vacuo at 40° C. for 12 hours. As a result, 55.7 grams (yield: 83%) of carnitinamide chloride with a purity of 99.6 wt % (with the remainder being carnitine nitrile chloride) was obtained. Also, 7.3 grams of secondary crystals (58.4 Wt % carnitinamide chloride, 0.7 wt % carnitine hydrochloride and 40.9 wt % carnitine nitrile chloride) was obtained from the filtrate. Using the secondary crystals as a raw material, a reaction was carried out in the reaction system described in (1) at a flow rate of 6.0 g/hr, and then the reaction product was purified. As a result, 6.1 grams of carnitinamide chloride (with a purity being 99.5 wt % and the remainder being carnitine nitrile chloride) was obtained. Yield of the total of the thus-isolated carnitinamide chlorides was 92%.

Example 9

(1) Reaction: A glass reaction tube with an inner diameter of 10 mm, equipped with a jacket, was filled with 3.0 grams of a modified manganese dioxide containing tin (atomic ratio of tin/potassium/manganese =0.02/0.08/1), which was prepared in the same manner as in Example 2 except that tin sulfate was used instead of vanadium sulfate and was uniformly pulverized and classified to have 10 to 20 mesh. Hot water at 60° C. was passed through the jacket. A raw material solution obtained by mixing 10 wt % of carnitine nitrile hydrochloride with 90 wt % of water was passed through the reaction tube at a flow rate of 3.0 g/hr. 24, 120 and 210 hours after the start of passing the solution, conversion of carnitine nitrile chloride of the solution at the outlet of the reactor were 80.5, 82.0, and 83.0%, respectively, and selectivity of carnitinamide thereof was 99.0, 98.6, and 98.8%, respectively.

Example 10

(1) Catalyst Preparation: A solution obtained by dissolving 0.33 mol of manganese sulfate monohydrate in 215 ml of water and then mixing therewith 0.958 mol of concentrated sulfuric acid was rapidly poured under stirring at 75° C. into a solution of 0.398 mol of potassium permanganate in 220 ml of water. Stirring was further continued at 70° C. for two hours, and then at 90° C. for four hours, so that the mixture was aged. A suspension containing 0.007 mol of bismuth (III) oxide in 440 ml of water was rapidly poured into the mixture. The resulting mixture was stirred at room temperature for 30 minutes, and then the resulting precipitate was filtered and washed with 2000 ml of water four times to give a precipitate cake. The resulting cake was dried overnight at 110° C. to give 60 grams of a modified manganese dioxide. Contents of metal components in the modified manganese dioxide were measured, and the result was bismuth/potassium/manganese=0.01/0.09/1 (atomic ratio).

(2) Reaction: A glass reaction tube with an inner diameter of 10 mm, equipped with a jacket, was filled with 3.0 grams of the prepared modified manganese dioxide containing bismuth, which was uniformly pulverized and classified to have 10 to 20 mesh. Hot water at 60° C. was passed through the jacket. A raw material solution obtained by mixing 10 wt % of carnitine nitrile hydrochloride with 90 wt % of water was passed through the reaction tube at a flow rate of 3.0 g/hr. 24, 120, 210 and 600 hours after the start of passing the solution, conversion of carnitine nitrile chloride of the solution at the outlet of the reactor were 88.4, 86.1, 84.0, and 85.0%, respectively, and selectivity of carnitinamide thereof were 98.9, 98.6, 99.0, and 98.9%, respectively.

mercially available manganese dioxide in comparison with the present modified manganese dioxide which contained vanadium and was prepared in Example 2.

The invention claimed is:

1. A process for producing carnitinamide, which comprises hydrating carnitine nitrile represented by the following general formula (1) in a presence of a catalyst containing a manganese oxide, an alkali metal element and at least one element selected from the group consisting of bismuth, vanadium and tin:

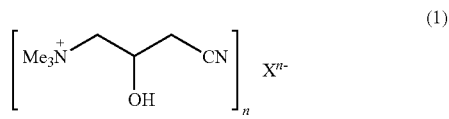

(1)

wherein $X^{n-}$ is an anion of a mineral acid or organic acid; and n is a positive integer excluding zero.

2. The process for producing carnitinamide, according to claim 1, wherein the alkali metal element comprises at least one element selected from the group consisting of sodium and potassium.

3. The process for producing carnitinamide, according to claim 1, wherein $X^{n-}$ in the general formula (1) is $Cl^-$.

TABLE 1

| Examples | Catalyst composition | Type of substrate salt | Carnitine nitrile (%) | | |
|---|---|---|---|---|---|
| | | | Conversion | Selectivity | Yield |
| Example 3 | Modified manganese dioxide containing vanadium | Hydrochloride | 96.7 | 99.7 | 96.4 |
| Example 4 | Modified manganese dioxide containing vanadium | Iodate | 94.4 | 99.7 | 94.1 |
| Example 5 | Modified manganese dioxide containing vanadium | Sulfate | 88.2 | 99.1 | 87.4 |
| Example 6 | Modified manganese dioxide containing vanadium | Nitrate | 95.1 | 99.4 | 94.5 |
| Example 7 | Modified manganese dioxide containing vanadium | Acetate | 90.7 | 99.1 | 89.9 |
| Comparative Example 1 | Concentrated hydrochloric acid | Hydrochloride | 91.8 | 85.1 | 78.1 |

TABLE 2

| Examples | Catalyst composition | Carnitine nitrile (%) | Reaction time (hr) | | | |
|---|---|---|---|---|---|---|
| | | | 24 | 120 | 210 | 600 |
| Example 8 | | Conversion | 93.2 | 91.7 | 90.5 | 86.2 |
| | Catalyst: vanadium/potassium/manganese | Selectivity | 98.5 | 98.3 | 98.4 | 99.5 |
| | Substrate: carnitine nitrile hydrochloride | Yield | 91.8 | 90.1 | 89.1 | 85.8 |
| Example 9 | | Conversion | 80.5 | 82.0 | 83.0 | |
| | Catalyst: tin/potassium/manganese | Selectivity | 99.0 | 98.6 | 98.8 | |
| | Substrate: carnitine nitrile hydrochloride | Yield | 79.7 | 80.9 | 82.0 | |
| Example 10 | | Conversion | 88.4 | 86.1 | 84.0 | 85.0 |
| | Catalyst: bismuth/potassium/manganese | Selectivity | 98.9 | 98.6 | 99.0 | 98.9 |
| | Substrate: carnitine nitrile hydrochloride | Yield | 87.4 | 84.9 | 83.2 | 84.1 |

BRIEF DESCRIPTION OF THE DRAWINGS

FIG. 1 shows the results of catalyst performance under batch-reaction conditions at 60° C. in connection with a com- 4. The process for producing carnitinamide, according to claim 2, wherein $X^{n-}$ in the general formula (1) is $Cl^-$.

* * * * *